US010660569B2

(12) United States Patent
Simons et al.

(10) Patent No.: US 10,660,569 B2
(45) Date of Patent: May 26, 2020

(54) APPARATUS, SYSTEM, AND METHODS FOR TARGETED MEMORY ENHANCEMENT DURING SLEEP

(71) Applicant: Teledyne Scientific & Imaging, LLC, Thousand Oaks, CA (US)

(72) Inventors: Stephen Simons, Raleigh, NC (US); Mario Aguilar-Simon, Chapel Hill, NC (US); Patrick Connolly, Cary, NC (US); Rolando Estrada, Chapel Hill, NC (US); Renee Shimizu, Durham, NC (US); Mary Whatley, Durham, NC (US)

(73) Assignee: TELEDYNE SCIENTIFIC & IMAGING, LLC, Thousand Oaks, CA (US)

(*) Notice: Subject to any disclaimer, the term of this patent is extended or adjusted under 35 U.S.C. 154(b) by 307 days.

(21) Appl. No.: 15/720,621

(22) Filed: Sep. 29, 2017

(65) Prior Publication Data

US 2018/0092600 A1    Apr. 5, 2018

Related U.S. Application Data

(60) Provisional application No. 62/403,318, filed on Oct. 3, 2016.

(51) Int. Cl.
*A61B 5/00* (2006.01)
*A61B 5/0476* (2006.01)
(Continued)

(52) U.S. Cl.
CPC .......... *A61B 5/6803* (2013.01); *A61B 5/0476* (2013.01); *A61B 5/4812* (2013.01);
(Continued)

(58) Field of Classification Search
CPC ... A61B 5/6803; A61B 5/4812; A61B 5/7282; A61B 5/0476; A61B 5/0482; A61N 1/36031; A61M 2230/04; A61M 21/02
See application file for complete search history.

(56) References Cited

U.S. PATENT DOCUMENTS

2006/0293608 A1*  12/2006  Rothman ............. A61B 5/0476
                                                                600/545
2014/0057232 A1    2/2014  Wetmore et al.
(Continued)

FOREIGN PATENT DOCUMENTS

WO    WO 2016/102602 A1    6/2016

OTHER PUBLICATIONS

Wilde et al., "Closed-loop transcranial alternating current stimulation of slow oscillations", Current Directions in Biomedical Engineering, 2015; 1, pp. 85-88.
(Continued)

*Primary Examiner* — Eric F Winakur
*Assistant Examiner* — Abid A Mustansir
(74) *Attorney, Agent, or Firm* — K&L Gates LLP

(57) ABSTRACT

Provided is an apparatus, system, and method for targeted memory enhancement. A computer processing circuit receives a plurality of electroencephalography (EEG) signals from a plurality of spatially separated EEG sensors located on the head of a subject that is asleep. A first process of the computer processing system determines a sleep state of the subject and upon determining that the subject is in sleep stage 2 or 3 based on a specific EEG signal, the processing system triggers a second process of the computer processing system that determines a transition event in the specific EEG signal, and upon detecting the transition event delivers an intervention to the subject designed to evoke a specific neurophysiological change to the subject.

16 Claims, 10 Drawing Sheets

(51) Int. Cl.
*A61N 1/36* (2006.01)
*A61B 5/0482* (2006.01)
*A61M 21/02* (2006.01)

(52) U.S. Cl.
CPC ........ *A61N 1/36031* (2017.08); *A61B 5/0482* (2013.01); *A61B 5/7282* (2013.01); *A61M 21/02* (2013.01); *A61M 2230/04* (2013.01)

(56) References Cited

U.S. PATENT DOCUMENTS

2015/0379878 A1   12/2015  Walter et al.
2017/0368348 A1*  12/2017  Le Van Quyen .... A61N 1/0408

OTHER PUBLICATIONS

Extended European Search Report for European Application No. 17194233.7 dated Mar. 8, 2018.

* cited by examiner

APPARATUS, SYSTEM, AND METHODS FOR TARGETED MEMORY ENHANCEMENT DURING SLEEP

CROSS-REFERENCE TO RELATED APPLICATIONS

This application claims the benefit of U.S. Provisional Application No. 62/403,318, filed Oct. 3, 2016, which is herein incorporated by reference in its entirety.

STATEMENT OF GOVERNMENTAL INTEREST

The subject matter described in the present disclosure was developed with U.S. Government support under DARPA RAM Replay program contract number W911NF-16-2-0007. The U.S. Government has certain rights in the subject matter.

FIELD OF TECHNOLOGY

This disclosure is directed generally to an apparatus, system, and method for a closed-loop system to enhance or potentially restore memory during sleep and/or improve skill acquisition in humans.

BACKGROUND

Memory replay refers to the process during sleep wherein brain activity representing previously learned experiences is reactivated in order to consolidate such activity into long-term memory. Conventional memory enhancement techniques that target the mechanism of memory replay have been studied in an academic context. One convention technique (Ken Paller of Northwestern University) has shown that playing sounds randomly during sleep can improve memory on simple tasks. This approach is known as targeted memory reactivation (TMR).

Other conventional techniques (Jan Born) have applied direct current neurostimulation in an open-loop fashion (e.g., not dependent on ongoing processes in the brain to improve the specificity of timing). Another technique (Flavio Frohlich) has targeted a different biomarker known as the sleep spindle using alternating current stimulation in a closed-loop system.

A challenge of using these conventional memory enhancement interventions is the inability to fully improve memory retention by targeting specific neurophysiological events that occur during sleep. These events may occur only at specific stages of sleep (e.g. deep sleep, REM sleep) and even more precisely only over short intervals (e.g. 500 ms). Conventional memory enhancement techniques do not provide real-time detection and delivery that enables precise targeting to biological phenomena as they occur. Furthermore, conventional memory enhancement techniques do not necessarily use targeted neurostimulation to locations demonstrated to be memory-type specific. It is therefore desirable to provide an apparatus, system, and method for applying memory enhancing interventions (e.g. sensory stimulation, direct current neurostimulation) based on the real-time detection of relevant biomarkers and which can also simultaneously titrate the delivery of these interventions based on real-time assessment of neurophysiological feedback in a closed-loop.

SUMMARY

In one aspect, the present disclosure provides an apparatus, system, and method for enhancing memory consolidation during sleep. The apparatus, system, and method leverages real-time detection of memory biomarkers to precisely deliver intervention signals (e.g. sensory or electrical neurostimulation) at optimal times during sleep.

More particularly, in another aspect, the present disclosure is directed to an apparatus, system, and method for improving memory retention by targeting specific neurophysiological events that occur during sleep. The apparatus comprises a head cap outfitted with sensors for recording electroencephalography (EEG) signals to record electrical activity of the brain and electrodes for delivering weak electrical current to the scalp, a processor. The apparatus may be used to implement methods for detecting cortical down-state to up-state transition events in the brain as well as for designing and coordinating stimuli (i.e. intervention signal) delivery. The apparatus use can be coordinated to enhance selected experiences such as by ensuring its use during a nap immediately following a training session. In a similar fashion, the apparatus can be used to deliver stimulation explicitly designed for the training objectives. For example, an intervention signal may be applied to an anatomical region of the head known to be involved in a specific type of memory or task (e.g., parietal lobe for spatial memory) or in the case of sensory stimulation, by using stimuli which are associated with previous learning and/or memory associated with previous learning.

In another aspect, a targeted method for memory enhancement is provided. The method comprises receiving, by a computer processing circuit, a plurality of electroencephalography (EEG) signals from a plurality of spatially separated EEG sensors located on the head of a subject that is asleep; determining, by a first process of the computer processing circuit, a sleep state of the subject; upon determining, by the computer processing circuit, based on a specific EEG signal that the sleep state of the subject is one of sleep stage 2 or sleep stage 3: triggering, by the computer processing circuit, a second process of the computer processing circuit; determining, by the second process of the computer processing circuit, a transition event of the specific EEG signal; and delivering, by the computer processing circuit, upon determining the transition event, an intervention signal to the subject designed to evoke a specific neurophysiological change to the subject.

In another aspect, a system for targeted memory enhancement is provided. The system comprises a plurality of spatially separated EEG sensors configured to be located on the head of a subject to generate a plurality of EEG signals; and a computer processing circuit configured to receive the plurality of EEG signals and to deliver an intervention signal designed to evoke a specific neurophysiological change to the subject based on a determined transition event, wherein the computer processing circuit is further configured to: determine that the subject is in one of a sleep stage 2 or a sleep stage 3 based on a specific EEG signal of the plurality of EEG signals, determine the transition event, wherein the transition event occurs during one of the sleep stage 2 or the sleep stage 3.

In yet another aspect, a targeted memory enhancement apparatus is provided. The apparatus comprises a plurality of spatially separated EEG sensors configured to be located on the head of a subject that is asleep, wherein the spatially separated EEG sensors are further configured to generate a plurality of EEG signals, wherein the plurality of spatially separated EEG sensors is for use with a targeted memory enhancement method, and wherein the targeted memory enhancement method comprises: determining the subject is in one of a sleep stage 2 or a sleep stage 3 based on a specific EEG signal; determining a neural biomarker of the specific EEG signal; and delivering, upon determining the neural biomarker, an intervention signal to the subject designed to evoke a specific neurophysiological change to the subject.

The foregoing summary is illustrative only and is not intended to be in any way limiting. In addition to the illustrative aspects and features described above, further aspects and features will become apparent by reference to the drawings and the following detailed description.

FIGURES

The novel features described herein are set forth with particularity in the appended claims. Various aspects, however, both as to organization and methods of operation may be better understood by reference to the following description, taken in conjunction with the accompanying drawings as follows:

Figure 9:
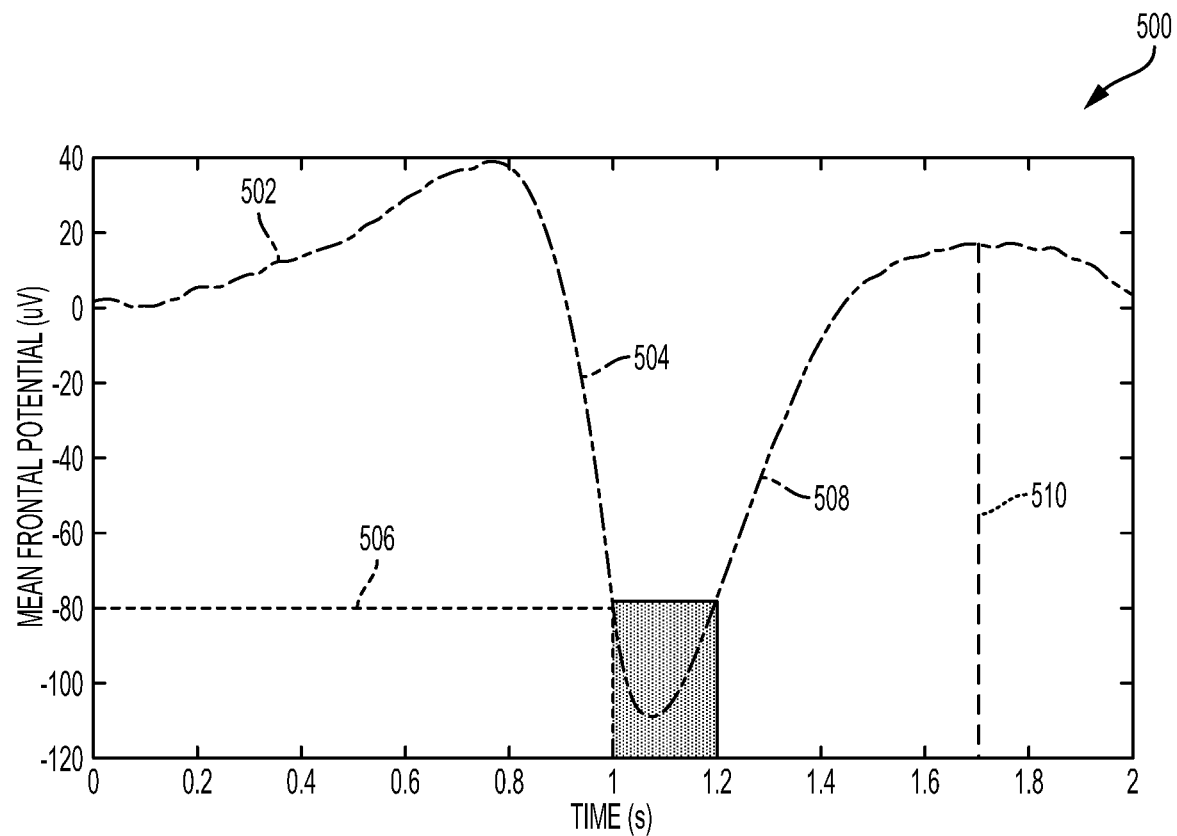

FIG. 9 graphically depicts a cortical down-state to up-state transition event in a specific digital EEG waveform according to various aspects of the present disclosure.

Figure 10:
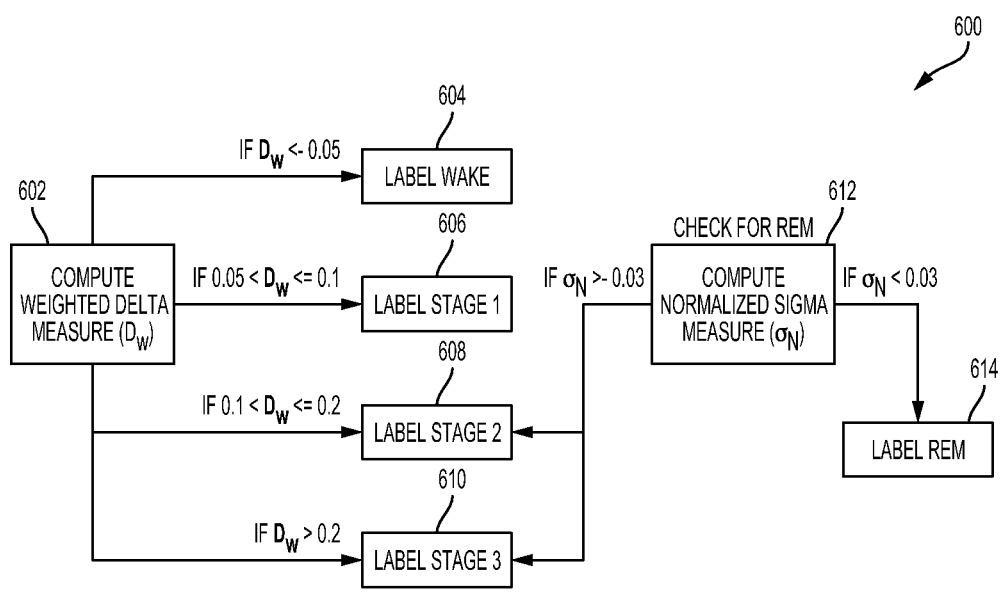

FIG. 10 is a flow diagram of a sleep stage detection algorithm according to various aspects of the present disclosure.

Figure 11:
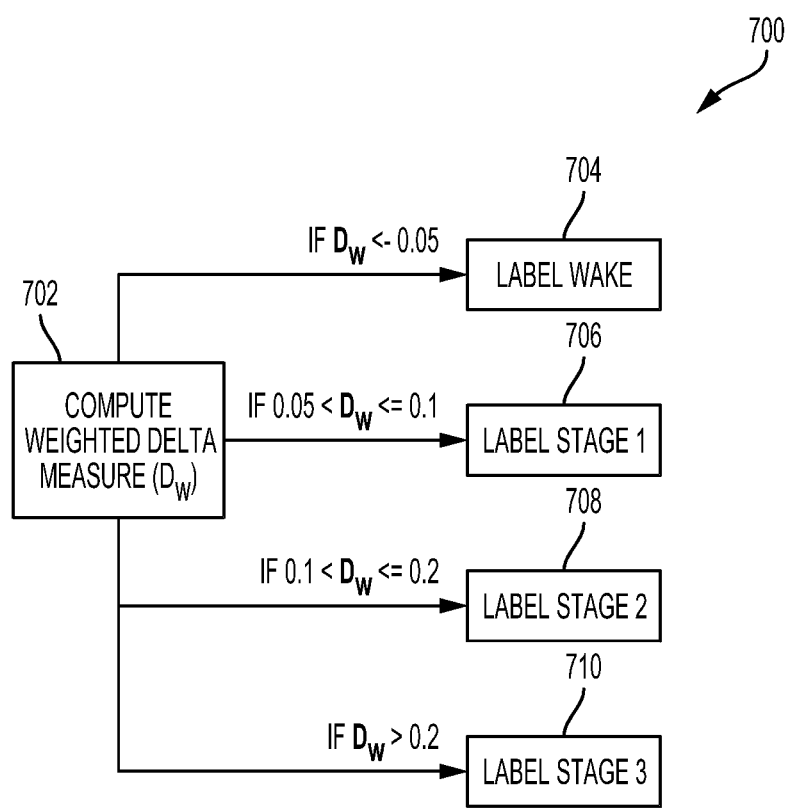

FIG. 11 is a flow diagram of a sleep stage detection algorithm that does not check for REM sleep stage according to one aspect of the present disclosure.

Figure 12:
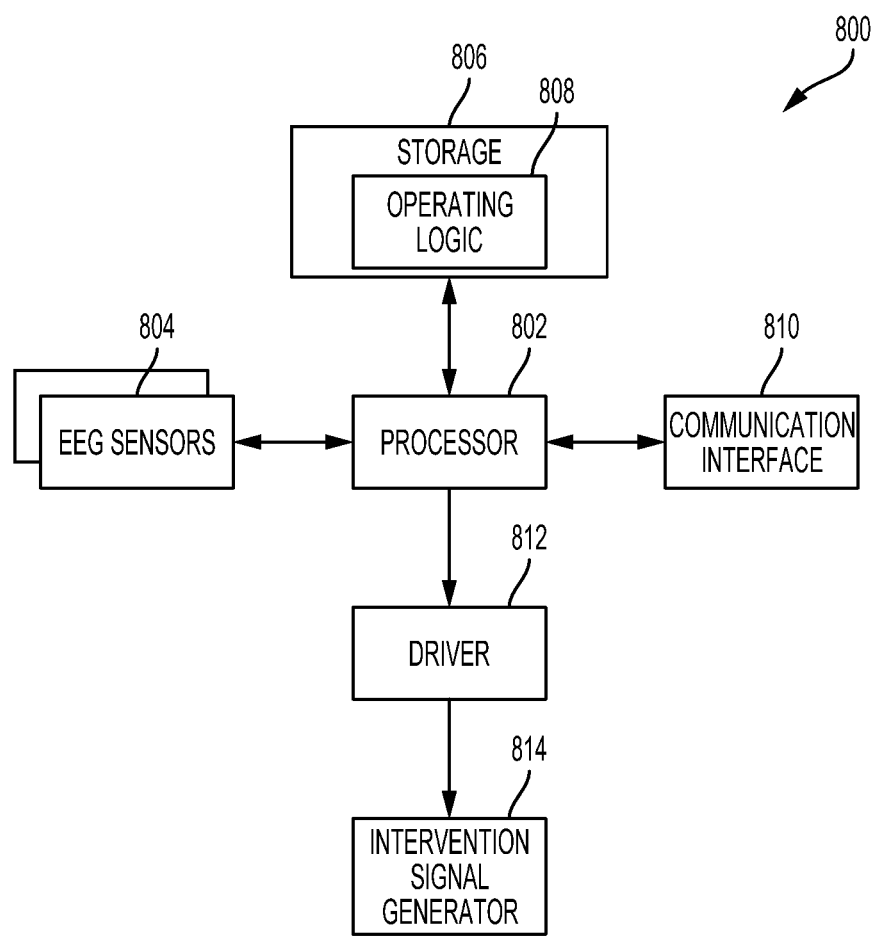

FIG. 12 illustrates an architectural or component view of a computing system that may be employed with the targeted memory enhancement process described in connection with FIGS. 1-11 according to various aspects of the present disclosure.

DESCRIPTION

In the following detailed description, reference is made to the accompanying drawings, which form a part hereof. In the drawings, similar symbols and reference characters typically identify similar components throughout the several views, unless context dictates otherwise. The illustrative aspects described in the detailed description, drawings, and claims are not meant to be limiting. Other aspects may be utilized, and other changes may be made, without departing from the scope of the subject matter presented here.

Before explaining the various aspects of the present disclosure in detail, it should be noted that the various aspects disclosed herein are not limited in their application or use to the details of construction and arrangement of parts illustrated in the accompanying drawings and description. Rather, the disclosed aspects may be positioned or incorporated in other aspects, variations and modifications thereof, and may be practiced or carried out in various ways. Accordingly, aspects disclosed herein are illustrative in nature and are not meant to limit the scope or application thereof. Furthermore, unless otherwise indicated, the terms and expressions employed herein have been chosen for the purpose of describing the aspects for the convenience of the reader and are not to limit the scope thereof. In addition, it should be understood that any one or more of the disclosed aspects, expressions of aspects, and/or examples thereof, can be combined with any one or more of the other disclosed aspects, expressions of aspects, and/or examples thereof, without limitation.

Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various aspects will be described in more detail with reference to the drawings.

Certain signals in the brain that occur in non rapid eye movement (NREM) sleep are correlated with memory retention. Under a conventional classification of stages of sleep which includes five stages, NREM refers to sleep stages 1 to 4. NREM sleep may be followed by the fifth stave, namely, rapid eye movement (REM) sleep. A sleep cycle can be defined as the amount of time necessary for an individual to transition through the five stages of sleep. In one aspect of the present disclosure, some signals of interest include down-state to up-state transition events. These transition events are electrical signals generated by the brain of an individual which may be detected in stage 2 or stage 3 sleep. The stages of sleep may include specific brain waves (i.e. detectable EEG waveforms) which may be classified based on waveform frequency. One conventional frequency classification includes delta waves ranging from 0 to 4 Hertz (Hz), theta waves ranging from 4 to 8 Hz, alpha waves ranging from 8 to 13 Hz, beta waves ranging from 13 to 30 Hz, and gamma waves ranging from 30 to 40 Hz. However, other suitable frequency classifications may also be used. For example, in another classification, delta waves may range from 1 to 4 Hz, alpha waves may range from 8 to 12 Hz, and gamma waves may range from 25 to 50 Hz. Stage 2 sleep includes certain characteristic EEG waveform patterns such as sleep spindles and K complexes. These characteristic EEG waveform patterns can be referred to as biomarkers.

Sleep spindles are bursts of waves with a typical frequency ranging from 11 to 16 Hz, each typically occurring for a duration of between 0.5 to 1.5 seconds. Sleep spindles can arise from thalamocortical oscillations. K-complexes are high voltage biphasic waves (i.e. high amplitude in terms of electrophysiological potential) comprising a sharp negative wave followed by a positive high voltage slow wave. The duration of a K-complex should exceed 0.5 seconds. Stage 3 sleep also includes certain characteristic EEG waveform patterns such as large amplitude slow oscillations (slow waves). Slow waves refer to waves ranging in frequency from 0.5 to 2 Hz with amplitudes exceeding 75 microvolts ($\mu V$). K-complexes and slow waves are both examples of transition events. Such transition events may be detected and used as an indication of neural plasticity. In other words, the processes of long-term memory consolidation can be particularly effective during cortical up-states that follow these transition events. Thus, in another aspect of the present disclosure, the delivery of targeted interventions precisely at the occurrence of these transition events can result in significant gains in memory enhancement. As discussed in further detail below, the interventions may be the delivery of either a weak electrical stimulus to a specific area of the head, or a sensory stimulation (e.g. a sound) delivered precisely at the time of the cortical transition event for improving memory consolidation. The present disclosure applies a closed-loop approach to targeted memory enhancement, which includes the detection of transition events in real-time.

In another aspect, for a particular subject (e.g. a human participant), the signals of interest are detected through a small set of electrodes that are configured to be applied noninvasively to the scalp of the subject. These signals are processed with a set of algorithms in real-time to achieve two functions that are necessary for the accurate and effective delivery of interventions. The signals may be EEG signals and the small set of electrodes may form a headband or headset of spatially separated EEG sensors. First, a sleep stage detection algorithm is used to classify the sleep stage of the subject using, for example, a hypnogram. The sleep stage detection algorithm can determine that the subject is in sleep stage 2 or 3. It may be easy to erroneously classify slow oscillations in other stages (i.e. stage 1, 4, or REM sleep) as transition events. Therefore, in order to avoid significant numbers of false positives, the sleep stage detection algorithm may be used to gate or trigger the transition events detection algorithm. Second, the transition events detection algorithm is used to identify a transition event or another suitable neurophysiological biomarker. Identification of the transition event can be quickly followed by application of the intervention. In other words, there can be low latency between identification and application, such as between 50 and 200 milliseconds (ms).

The applied intervention may be designed to impact a specific type of memory. In one aspect, the targeted memory enhancement system of the present disclosure selects an appropriate intervention which is configured to achieve the designed impact. For example, as described in further detail below, the selected intervention signal may be an auditory cue that is associated with the memory which is targeted for enhanced memory consolidation. The associated auditory cue is effective at enhancing consolidation of the associated memory, which may be indicative of increasing the probability of synchronously activating the interconnected neurons corresponding to the memory during a cortical up-state of a subject. Additionally or alternatively, the system of the present disclosure may also select an electrical stimulation as the selected intervention. Certain parameters of the electrical stimulation, such as the location(s) (which is specific for different types of memory), frequency (which may be specific to the subject), and the duration of electrical current delivery can be specified by the system. Other specific sensory stimulus may be used as the intervention. While the system has been tested on 90 minute naps, the system is also usable during overnight sleep, which would likely be an equally if not more efficacious application of the system.

Accordingly, in one aspect, the present disclosure includes a device that when worn by an individual during sleep will improve memory consolidation for events or tasks performed by the individual prior to sleep by delivering an intervention synchronized to a cortical up-state of the individual's brain. Usage of the device can be temporally coordinated with the daily activities of the individual. For example, to enhance memory recall of a selected experience, the individual may use the device during a nap immediately following the selected experience. Alternatively, the individual may use the device during a nap immediately preceding a training session. The device may comprise an EEG sensor headset comprising a number of spatially separated electrodes, a computer processing circuit, and methods for designing and coordinating delivery of an intervention signal. The EEG sensor headset is configured to monitor and electrically stimulate brain activity of the individual wearing the headset.

In another aspect of the present disclosure, a set of headphones may be used to deliver sounds (i.e. auditory intervention signals) at specific times that are determined by the transition events detection algorithm or another suitable algorithm executed by the computer processing circuit. Execution of the transition events detection algorithm by computer processing circuit comprises processing sensed/captured signals from the brain monitoring electrodes to detect down-state to up-state transition events and applying an auditory or electrical intervention signal contemporaneously with the commencement of the detected cortical up-state. Prior to execution of the transition events detection algorithm, the computer processing circuit also executes the sleep stage detection algorithm to determine that the individual is in sleep stage 2 or 3. Accordingly, only transition events detected while the individual is in sleep stage 2 or 3 are permitted to trigger an intervention signal. One example of a method to deliver the intervention signal includes coordinating training material to contain pre-specified auditory stimuli presented during a training session for the individual, where the auditory stimuli is played synchronously with transition events occurring while the individual is in sleep stage 2 or 3 during a sleeping session.

In various aspects, the apparatus, system, and method according to the present disclosure specifically uses a closed-loop methodology to specifically deliver interventions at optimal times to target transition events. The closed-loop methodology refers to an approach to targeted memory enhancement comprising delivering interventions synchronously with naturally occurring neural oscillations (e.g. slow oscillations such as K-complexes and slow waves in stage 2 and stage 3 sleep, respectively). In other words, the closed-loop methodology of the present disclosure uses intervention signals that are phase-dependent on an individual's natural neural oscillations such that the intervention signals are delivered during a cortical up-state of the individual. The cortical up-state follows a transition event, which is a neural biomarker shown to have great importance in memory consolidation. Moreover, the present disclosure includes the functions of performing a complete classification of non-REM sleep (which provides specificity into the types of phenomenon that can be targeted) as well as using targeted neurostimulation and/or sensory stimulation.

In one aspect, the present disclosure provides targeted memory enhancement. The applications are diverse and may include, for example: improving spatial memory of new environments (e.g., a new city), improving recollection of conversational content (e.g., lectures), increasing the rate of language learning, and increasing the rate of learning of visual information. The intervention signals used in the present disclosure may be tailored to the particular selected application. In particular, by applying a tailored intervention signal that is associated with the memory to be enhanced during a cortical up-state, the intervention signal may promote memory reactivation and consolidation by increasing the probability of activating interconnected neurons of the memory trace corresponding to the memory to be enhanced.

In various aspects, the present disclosure is directed to a well characterized property of the human nervous system (and the nervous systems of other mammals) for memory formation. The property, known as memory replay, refers to a hypothesized mechanism for information transfer from the hippocampus to the cerebral cortex wherein after experiences are encoded in the hippocampus in short-term memory, they are reactivated (e.g. replayed) during sleep in order to consolidate them for long-term storage in the cortex. This memory reactivation may recur transiently to strengthen neural connections (e.g. interconnected neurons of the memory trace that is being reactivated). Such memory reactivation may be reflected by the interaction of cortical slow oscillations (e.g. K-complexes and slow waves), thalamic sleep spindles and hippocampal sharp wave ripples (SWR). Accordingly, a targeted intervention signal delivered in a cortical up-state following a detected transition event in conjunction with the interaction of thalamic sleep spindles and SWR may foster and/or enhance memory reactivation.

According to general principles of neuroscience, the human brain includes deep brain structures and surface brain structures. The surface brain structures generically can be called the cerebrum and more specifically, the cerebral cortex. There are areas of the cerebral cortex that are functionally and topographically distinct. For example, the area of the cerebral cortex that is located at the back of the human head is responsible for processing vision. The area of the cerebral cortex that is located at the middle portion of the head is responsible for the motor and tactile sensory functions. The area of the cerebral cortex that is located toward the forehead is responsible for higher level cognition, decision making, and similar functions. The hippocampus is a midbrain structure which has been shown to be critical for memory and maintains extensive connections to the cerebral cortex to coordinate the learning, modification and storage of memory.

The function of the hippocampus could be analogized to random access memory in modern computers. According to one theory, new memories are first encoded in the hippocampus. Thus, during the day as an individual goes about their business, such as walking in a new city and observing new buildings, information from the occipital lobe of the cerebral cortex is relayed to the hippocampus to be stored temporarily (where the relayed information generates a specific pattern of activity in the hippocampus). Continuing the modern computer analogy, the hippocampus acts as a short-term memory buffer, rather than as a long term memory structure for storing information. Because the hippocampus does not act as the structure for long-term storage of memory, the hippocampus is theorized as sending the temporarily encoded information to the cerebral cortex for consolidation and long-term storage. This process references the memory replay property described above, upon which various aspects of the present disclosure are based. Furthermore, it is fairly well understood that there are certain oscillatory signals in the brain that correspond to the memory replay process and several of these oscillatory signals can be utilized by the present disclosure described herein. For example, such oscillatory signals or patterns include hippocampus SWR, theta, and gamma oscillations.

Figure 1:
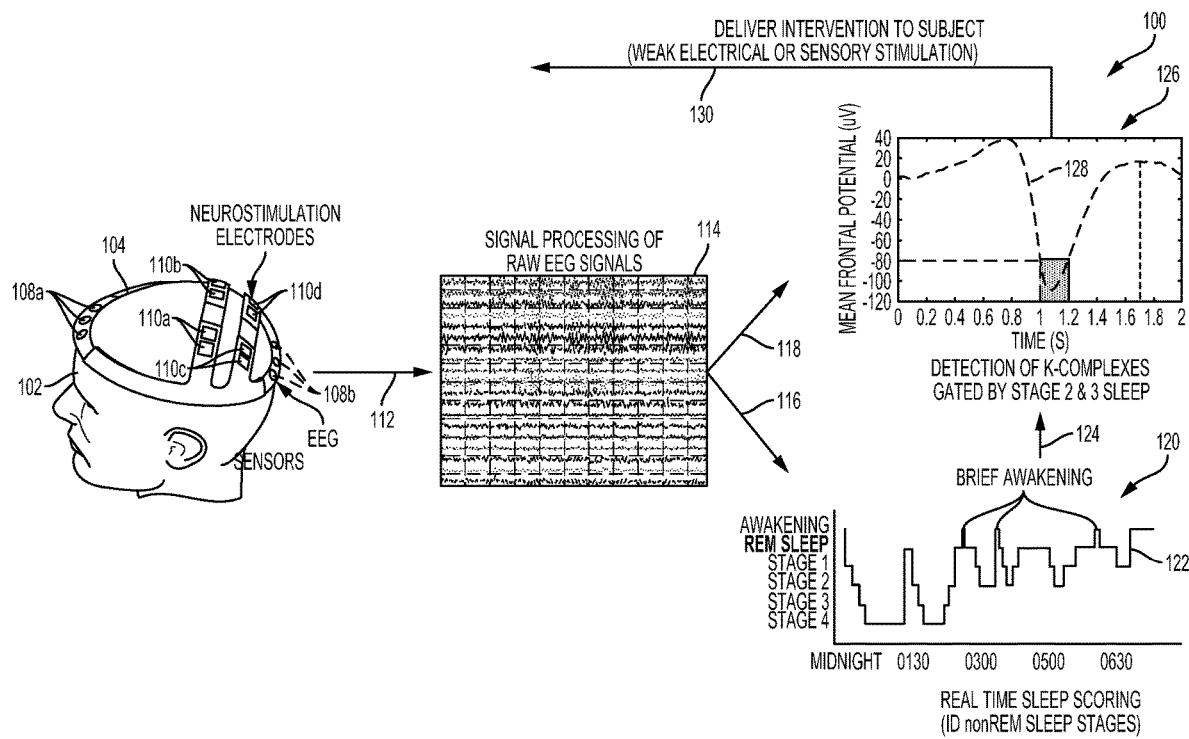
FIG. 1 is a diagram that represents the closed-loop operation of a targeted memory enhancement system according to various aspects of the present disclosure.

Turning now to FIG. 1, there is shown a diagram 100 that represents a closed-loop process for targeted memory enhancement according to various aspects of the present disclosure. In one aspect, the process includes sensing activity in the cerebral cortex of a subject 102 using EEG. The subject 102 wears an EEG headband or headset 104 having a relatively high density set of EEG electrodes that cover the surface of the scalp. The EEG electrodes may be arranged in a 32-channel system, for example. The headset 104 comprises a plurality of EEG sensors 108a, 108b. Throughout this disclosure, the EEG sensors also may be alternatively referred to as EEG electrodes or EEG channels.

A first set of EEG sensors 108a is placed near the frontal lobe of the cerebral cortex and a second set of EEG sensors 108b is placed near the occipital lobe of the cerebral cortex.

In another aspect, only the first set of EEG sensors 108a are used such that the headset 104 comprises only the EEG sensors 108a positioned on the forehead of the subject 102. This enables the EEG sensors 108a only to contact the head of the subject 102 in areas where there is no hair on the head. In other words, the EEG sensors 108b (shown in dashed line format) may not be provided. When only the first set of EEG sensors 108a are provided such that only brain activity near frontal channels (corresponding to areas near the frontal lobe) is detected, executing the sleep stage detection algorithm may not involve alpha wave activity, as described further below. In fact, measurements of alpha wave activity may not be prominent on frontal channels. The headset 104 also comprises sets of neurostimulation electrodes 110a, 110b, 110c, 110d for applying an electrical stimulation intervention signal. Each of the neurostimulation electrode sets 110a-d may comprise three electrodes or some other suitable number of electrodes. The neurostimulation electrode sets 110a-d may be positioned proximal to the parietal lobe. In another aspect, the sets of neurostimulation electrodes 110a-d are positioned on another area of the head of the subject 102, or not provided at all.

In various aspects, additional or fewer EEG electrodes 108a-108b or neurostimulation electrodes 110a-d may be employed without departing from the scope of the present disclosure. In one aspect, three EEG sensors 108a are placed over the frontal lobe of the cerebral cortex for implementation of the sleep stage detection algorithm. EEG sensors 108b placed over the occipital lobe of the cerebral cortex may be unnecessary for the sleep stage detection and transition events detection algorithms. However, in alternative aspects, a suitable number of occipital EEG sensors 108b, such as three, are positioned over the occipital lobe.

While the subject 102 sleeps, EEG signals 112 can be sensed by the EEG sensors 108a-b based on electrical activity from the brain of the subject 102. Once the raw EEG signals 112 are collected, the EEG signals 112 are provided to a digital signal processing circuit to process the raw EEG signals 112. The computer processing circuit described above may comprise the digital signal processing circuit. Based on the collected EEG signals 112, the digital signal processing circuit produces digital EEG waveforms 114 for subsequent analysis. The computer processing circuit is configured to execute or implement specific algorithms for this analysis. Specifically, in one aspect, the computer processing circuit implements and executes the sleep stage detection algorithm and transition events detection algorithm described above. The computer processing circuit may also execute other suitable algorithms. The sleep stage detection algorithm comprises decoding the digital EEG waveforms 114 for determination of what stage of sleep the subject 102 is in.

The present disclosure classifies stages of sleep into stages 1 through 4 (NREM sleep) and REM sleep. However, the stages of sleep can also be classified into stages 1 through 3. Those skilled in the art will appreciate that NREM sleep can be further classified into light and deep stage sleep. These light and deep stages of sleep can be labeled according to either the classification into stages 1 to 3 or into stages 1 to 4. Other suitable classifications may also be used. Each sleep stage can be characterized by unique waveforms and patterns that describe the activity in the brain of the subject 102. As described above, for the purpose of targeted memory enhancement with respect to the memory replay process, the transition events detection algorithm may comprise analyzing only the brain behaviors (e.g. K-complexes and slow waves) thought to occur during stage 2 and stage 3 sleep. In short, it can be necessary to know which stage of sleep the subject 102 is in for targeted memory enhancement.

The present disclosure provides a sleep stage detection algorithm 116 to effectively detect in real time the stage of sleep of the subject 102. In one aspect, the sleep stage detection algorithm 116 involves generating a hypnogram 120 which comprises a graph 122 to represent the stages of sleep as a function of time. One or more suitable polysomnography techniques, which may include consideration of the weighted delta measure and normalized sigma measure described further with reference to FIGS. 10 and 11, are used to generate the hypnogram 120. EEG, electrooculogram (EOG), and electromyography (EMG) measurements can be used to score or classify a polysomnographic record of sleep into sleep stages. Such sleep stages are depicted in the hypnogram 120 and in more detail with respect to the hypnogram 400 shown in FIG. 8.

As shown in the hypnogram 120 in FIG. 1 and described in more detail with reference to the hypnogram 400 in FIG. 8, the stages of sleep are provided along the vertical axis and time is provided along the horizontal axis. The hypnogram 120, 400 provides an easy way to present the recordings of brain wave activity from a digital EEG waveform 114 during a period of sleep according to the sleep stage classification of the present disclosure. The wake state, REM sleep, and NREM sleep (comprising stages 1 to 4) of the subject 102 are determined and displayed on the hypnogram 120, 400, as indicated along the vertical axis of the hypnogram 120, 400. As previously described, NREM sleep can be classified into three stages rather than the four stages depicted in hypnogram 120, 400. In such three stage NREM classifications, the 4th stage of NREM sleep may be subsumed within stage 3. Furthermore, stage three as defined in three stage NREM classifications can be labeled slow wave sleep (SWS) and is the deepest stage of sleep.

Upon detecting the sleep stage of the subject 102, the sleep stage detection algorithm 116 triggers or gates 124 the down-state to up-state transition events detection algorithm 118 to detect a specific signal 126 o interest in the digital EEG waveform 114. In one aspect, the signal 126 of interest comprises a down-state to up-state transition event 128. Upon detecting the down-state-to-up-state transition event 128 signal, the transition events detection algorithm 118 may deliver an intervention signal 130 to the subject 102. Detection of the transition event 128 signal is further described with reference to FIG. 9. The intervention signal 130 may be a weak electrical signal or sensory stimulation provided to the neurostimulation electrodes 110a-d. When the applied intervention signal 130 is sensory stimulation, such sensory stimulation may be an auditory stimulation or cue, which may be associated with the targeted memory. Additionally or alternatively, the sensory stimulation intervention signal 130 can be an olfactory stimulation or a gustatory stimulation, which also may be associated with the targeted memory. Various parameters of the sensory stimulation, such as volume of an auditory stimulation or potency of an olfactory stimulation may be selected. When the applied intervention signal 130 is electrical stimulation, parameters such as location, frequency and duration of electrical current delivery may be specified. The intervention signal 130 could be applied by the headset 104 or by an external apparatus, such as, for example, headphones for delivering an auditory intervention signal 130 or a spray bottle containing an olfactory substance for delivering an olfactory intervention signal 130. Moreover, the intervention signal 130 could comprise both an electrical signal and one or more sensory stimulations.

In one aspect, the intervention signal 130 can be an auditory cue of a predetermined length. In one example, the auditory cue 130 is in the form of a very short sound, such as 500 milliseconds long. Other suitable temporal lengths can be used as well. Auditory cues 130 can be experience-specific, relating to the type of memory being targeted for enhancement. For example, the subject 102 may be trained on a navigation task comprising walking through a virtual environment such as a virtual rendering of a city neighborhood. During training, every time the subject 102 crosses a boundary that is critical between two different zones of the virtual environment, a specific sound having a contextual attachment to the type of zone that the subject 102 is crossing into can be played. For example, when the subject 102 walking from a store (the first zone) crosses a sidewalk (the boundary) into a park (the second zone) and hears a dog barking, the dog barking sound will be associated with the spatial memory of entering the park. A dog barking auditory cue 130 can be used for targeted memory enhancement of memories corresponding to this experience during memory replay. Such corresponding memories could include the spatial location of the park relative to the virtual city neighborhood. Accordingly, the auditory intervention signal 130 is effectively replayed when the subject 102 is asleep and the brain of the subject 102 is engaged in memory replay during a cortical up-state. The auditory intervention signal 130 can be configured to be an appropriate length and normalized intensity. Continuing the example of the dog barking auditory cue 130, the auditory cue 130 can comprise a sequence of multiple types of memory associated sounds. The auditory cue 130 could comprise, for example, the sound of a park gate opening followed by a dog barking sound.

A weak electrical current intervention signal 130 can be applied to various specific areas of the brain in order to target selected functions that are topographically segregated in the brain. For example, if the subject 102 is trying to learn a spatial task, which involves the parietal lobe of the brain, the weak electrical current intervention signal 130 can be applied to parietal lobe in a specific pattern. One specific pattern may be a frequency pattern that matches the brain's natural oscillations relative to the parietal lobe. In this case, the intervention signal 130 may be targeted to enhance spatial memories associated with the spatial task to be learned. It will be appreciated that the intervention signal 130, whether applied as sensory stimulation or weak electrical current, may be applied individually or simultaneously to the subject 102. In other words, the intervention signal 130 may be applied to the neurostimulation electrodes 110a-d individually/selectively or simultaneously. The intervention signal 130 may trigger or promote memory reactivation and consolidation related to the memory to be enhanced. As described throughout the present disclosure, applying an intervention signal 130 that constitutes a cue for a memory to be more effectively reactivated and consolidated can be delivered at the right time (i.e. during a cortical up-state) for targeted memory enhancement.

In one aspect, the intervention signal 130 is applied precisely at the occurrence of the cortical up-state following a detected transition event 128 in stage 2 or stage 3 sleep. When the subject 102 is asleep, the brain of the subject 102 oscillates between states of excitability and states of less excitability. Accordingly, the intervention signal 130 can be timed for application subsequent to a detected transition event 128 such that the intervention signal 130 is applied when the brain of the subject 102 is an excitable state. It can be less effective to apply targeted memory enhancement when the brain is in a less excitable state. Thus, to improve reactivation and consolidation of a new memory, the functional and structural integrity of the neurons corresponding to the new memory should be altered during cortical up-states, when the corresponding neurons are most excitable. In sum, to precisely and more effectively impact memory reactivation and consolidation, the intervention signal 130 may be delivered during a cortical up-state, where the interconnected neurons of the memory trace corresponding to the new memory are most excitable.

Stimulating the neurons at the onset of the cortical up-state with the intervention signal 130 may be a particularly effective means of promoting synchronous activation of the corresponding interconnected neurons, which may activate a neural cascade involving the memory trace associated with the new memory. In other words, applying the intervention signal 130 at the cortical up-state onset may beneficially align the targeted memory enhancement (as represented by the applied intervention signal 130) with the brain's natural oscillation to an excited state (i.e. neuroplasticity for memory consolidation), which may support the brain's natural memory replay mechanism. Therefore, it is desirable to detect the transition event 128 for intervention signal 130 application at the commencement of the cortical up-state. The intervention signal 130 is therefore applied to the subject 102 according to a closed-loop methodology for targeted memory enhancement such that the intervention signal 130 is delivered in alignment with natural neural oscillations of the subject 102.

The down-state to up-state transition event 128 can be very robust and readily detected in stage 2 and 3 sleep. As described above, in stage 2 sleep, the high voltage biphasic waves which include transition events 128 are called K-complexes. It should be understood that all k-complexes are down-state to up-state transition events 128, but not all down-state to up-state transition events 128 are K-complexes. The large amplitude waves which occur in stage 3 sleep are called slow oscillations or slow waves. Slow waves also include detectable transition events 128. Stage three sleep can be defined as a deep stage of sleep in which the brain is engaged in very slow rhythmic activity. During stage 2 and 3 sleep, the transition events detection algorithm may determine that the brain of the subject 102 exhibits a sufficiently large oscillation that constitutes a sufficiently large change in excitability to qualify as a down-state to up-state transition event 128.

FIGS. 2-6 illustrate various views of a targeted memory enhancement system 200 for detecting brain activity and stimulating the brain of an individual during predetermined sleep cycles to improve the memory replay for memories of events or tasks performed by the individual prior to sleeping according to various aspects of the present disclosure. As discussed above, memory replay comprises memory reactivation and consolidation. The targeted memory enhancement system 200 depicted in FIGS. 2-6 includes a subject 102 wearing a headset 204 comprising a first and second plurality of spatially separated EEG sensors 208a, 208b, neurostimulation electrode sets 210a, 210b, 210c, 210d, and a computer processing circuit 212. Each of the first and second plurality of spatially separated EEG sensors 208a-b, neurostimulation electrode sets 210-d, and computer processing circuit 212 may be positioned on or embedded in bands of the headset 204, as illustrated in FIGS. 2-6. The computer processing circuit 212 comprises a computing system having one or more microprocessor(s), digital signal processor, memory, input/output (I/O), analog-to-digital converter (ADC) circuits, digital-to-analog converter (DAC) circuits, and other features required of a functional computer to process EEG signals, execute the sleep stage detection algorithm 116 (FIG. 1), down-state to up-state transition events detection algorithm 118 (FIG. 1), and deliver the intervention signal 130, among other functions. The computer processing circuit 212 receives inputs comprising EEG signals from the EEG sensors 208a-b, processes these inputs, and converts them into digital EEG waveforms that may be employed by the sleep stage detection algorithm 116 and the transition events detection algorithm 118.

In one aspect, the spatially separated EEG sensors 208a, 208b of the targeted memory enhancement system 200 are configured to sense activity in the cerebral cortex of a subject 102 using EEG. As shown in FIGS. 2-6, the subject 102 wears the headset 204 having a relatively high density set of EEG electrodes that cover the surface of the scalp. The components of the headset may be arranged relative to the cerebral cortex of the subject 102. The neurostimulation electrodes 210a-d may be positioned near the occipital lobe of the cerebral cortex. Each of the neurostimulation electrode sets 210a-d, which may be positioned near the parietal lobe of the cortex (closer to the back of the head), may comprise three electrodes or some other suitable number of electrodes. The sets of neurostimulation electrodes 210a-d can also be positioned on another area of the head of the subject 102, or not provided at all (e.g. when an external apparatus is used for an auditory intervention signal, for example). The computer processing circuit 212 may be positioned near the central sulcus or parietal lobe of cerebral cortex (closer to the front of the head), or some other suitable area. The first plurality of spatially separated EEG sensors 208a may be placed near the frontal lobe of the cerebral cortex and the second plurality of spatially separated EEG sensors 208b may be placed near the occipital lobe of the cerebral cortex. In an alternative aspect, only the first plurality of spatially separated EEG sensors 208a is provided in the targeted memory enhancement system 200. The sleep stage detection algorithm 116, transition events detection algorithm 118 and other functions of the targeted memory enhancement system 200 may only require EEG signals from the first plurality of spatially separated EEG sensors 208a. The first plurality of spatially separated EEG sensors 208a may be configured to be positioned such that they contact only portions of the forehead or head of the subject 102 where there is no hair.

Figure 2:
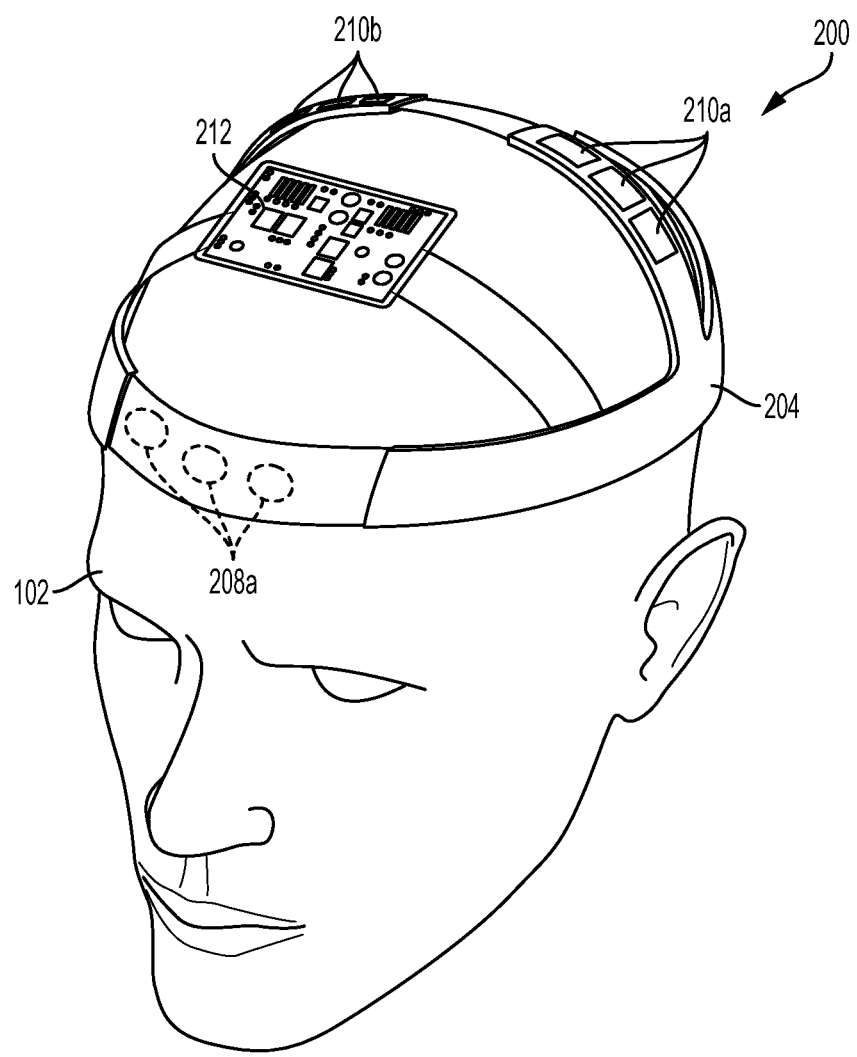
FIGS. 2-6 illustrate various views of hardware components of a targeted memory enhancement system for detecting brain activity and stimulating the brain during predetermined sleep cycles according to various aspects of the present disclosure.
Figure 3:
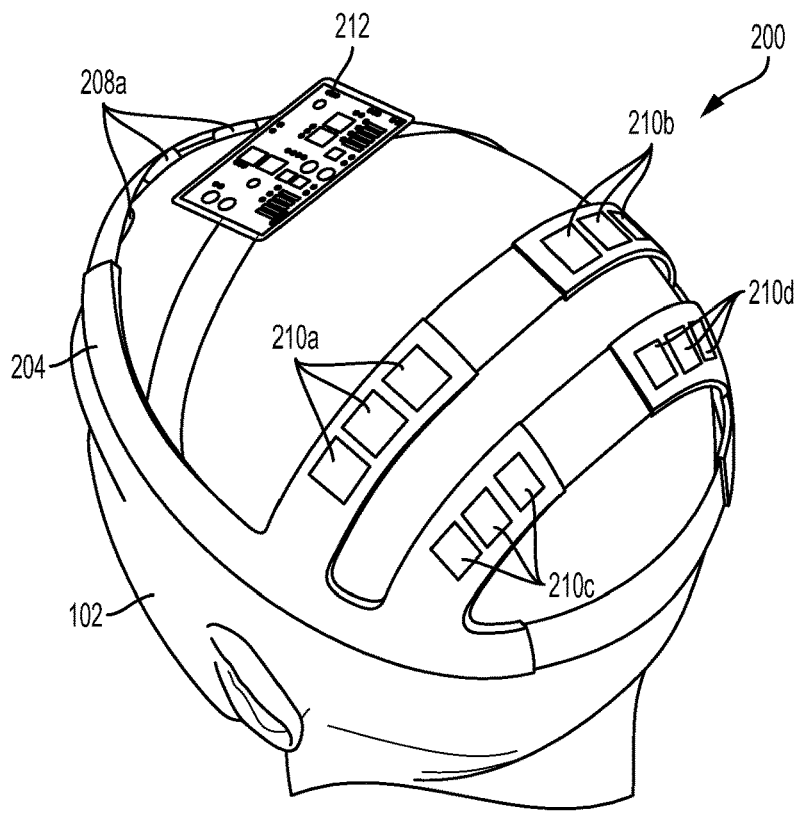

In various aspects, additional or fewer EEG electrodes 208a-b or neurostimulation electrodes 210a-d may be employed without departing from the scope of the present disclosure. FIGS. 2-3, for example, depict that the first plurality of spatially separated EEG sensors 208a comprises three EEG sensors positioned over the frontal lobe. In FIGS. 2-3, no second plurality of spatially separated EEG sensors 208b is positioned over the occipital lobe. As shown in FIG. 3, the first plurality of spatially separated EEG sensors 208a are placed on the interior side of the headset 204. The first plurality of spatially separated EEG sensors 208a may also be positioned in other suitable configurations or locations proximal to the frontal lobe. FIG. 2 is a frontal view of the targeted memory enhancement system 200 comprising the subject 102 wearing the headset 204 described above. In FIG. 2, the first plurality of spatially separated EEG sensors 208a are shown in dashed line. Additionally, in FIG. 2, only the sets of neurostimulation electrodes 210a-b are shown.

Figure 4:
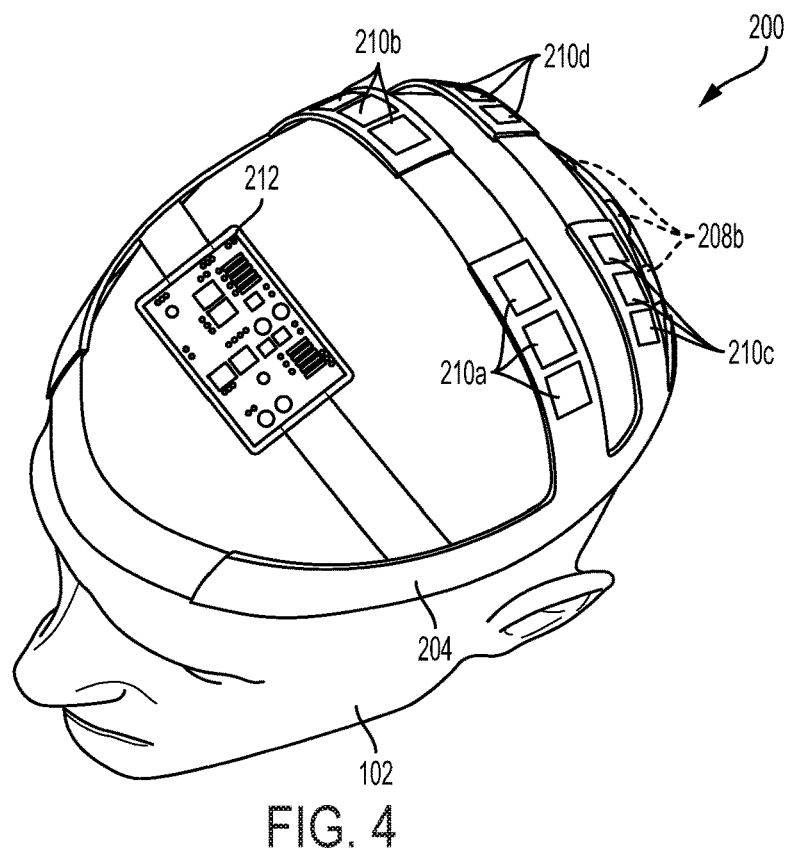
Figure 5:
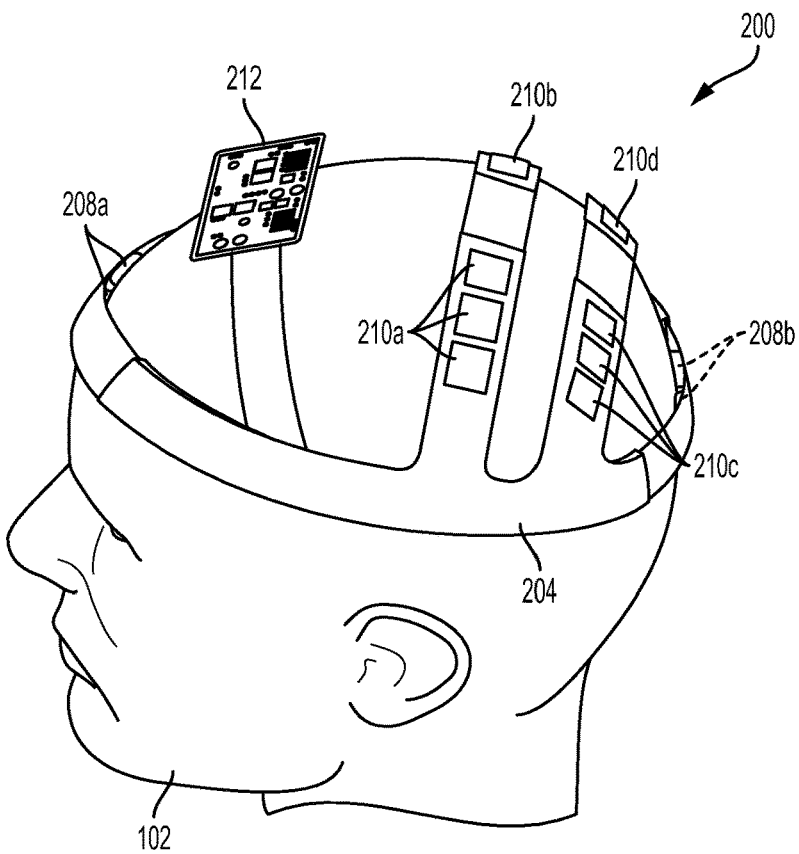
Figure 6:
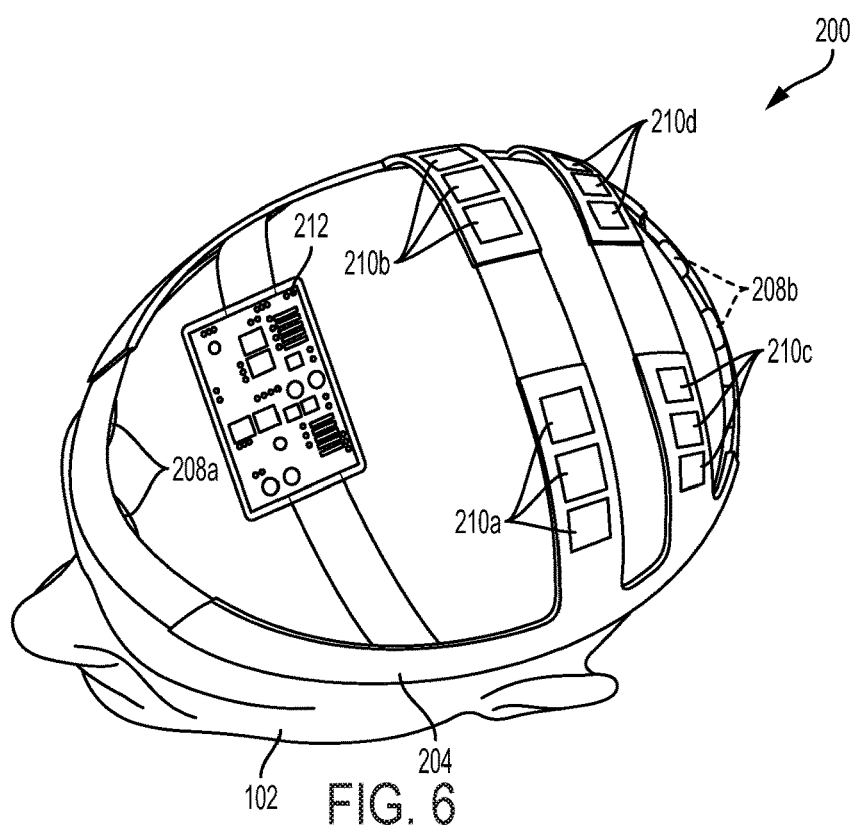

FIG. 3 is an occipital view of the targeted memory enhancement system 200 comprising the subject 102 wearing the headset 204 described above. In FIG. 3, the first plurality of spatially separated EEG sensors 208a is visible and positioned on the interior side of the headset 204. Also in FIG. 3, the second plurality of spatially separated EEG sensors 208b is not provided. FIG. 3 further depicts the sets of neurostimulation electrodes 210a-d. FIG. 4 is a side view of the targeted memory enhancement system 200 comprising the subject 102 wearing the headset 204 described above. In FIG. 4, the second plurality of spatially separated EEG sensors 208b is shown in dashed line. FIG. 5 is another side view of targeted memory enhancement system 200 comprising the subject 102 wearing the headset 204 described above. In FIG. 5, the first plurality of spatially separated EEG sensors 208a comprises two EEG sensors and the second plurality of spatially separated EEG sensors 208b is shown in dashed line. FIG. 6 is yet another side view of targeted memory enhancement system 200 comprising the subject 102 wearing the headset 204 described above. In FIG. 6, the first plurality of spatially separated EEG sensors 208a comprises two EEG sensors and the second plurality of spatially separated EEG sensors 208b are also shown in dashed line.

Referring now to FIGS. 1-6, in one aspect, the EEG signals 112 (FIG. 1) are sensed by the EEG sensors 208a-b while the subject 102 sleeps. Once the raw EEG signals 112 are collected, they are provided to the digital signal processor of the computer processing circuit 212 where the raw EEG signals 112 are processed to produce digital EEG waveforms 114 (FIG. 1). The digital EEG waveforms 114 (as described further with reference to the plurality of digital EEG waveforms 300 depicted in FIG. 7) are provided to the sleep stage detection algorithm 116 to decode the digital EEG waveforms 114, 300 and determine the stage of sleep of the subject 102. Upon detecting the stage of sleep of the subject 102, the transition events detection algorithm 118 detects a down-state to up-state transition event 128 (FIG. 1), as further described with reference to the graphical depiction 500 of a specific EEG signal 502 of interest depicted in FIG. 9. Upon detecting the down-state to up-state transition event 128, the computer processing circuit 212 delivers an intervention signal 130 to the subject 102 via the neurostimulation electrodes 210a-d. The intervention signal may be applied to the neurostimulation electrodes 210a-d individually or simultaneously.

Figure 7:
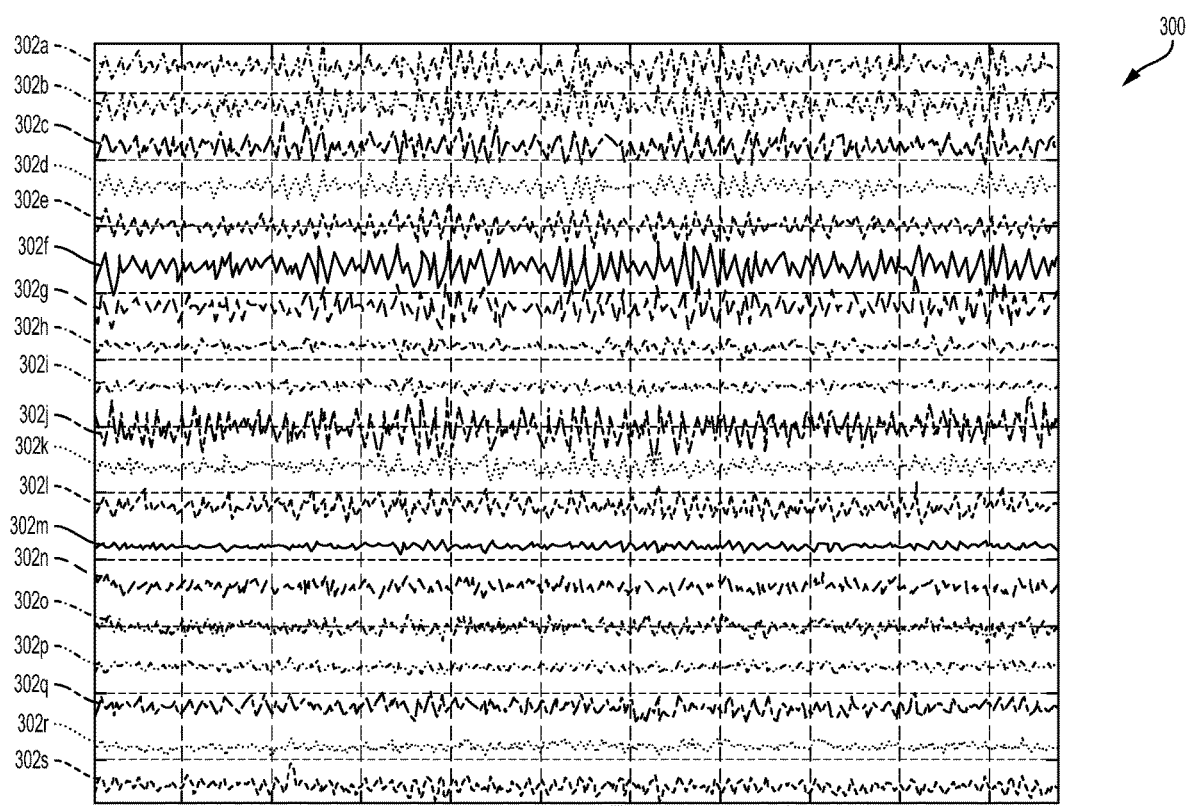
FIG. 7 is a diagram of a plurality of EEG signals that are sensed by a plurality of EEG sensors according to various aspects of the present disclosure.

FIG. 7 is a diagram of a plurality of digital EEG waveforms 300 that are sensed by a plurality of EEG sensors according to various aspects of the present disclosure. With reference to FIGS. 1-7, each of the first and second plurality of spatially separated EEG sensors 208a-b (in the headset 204 worn by the subject 102) detects the raw EEG signals 302a-s while the subject 102 sleeps. Each raw EEG signal 302a-s may correspond to a channel of the EEG sensors. The raw EEG signals 302a-302s can be amplified by an analog amplifier for further processing by the computer processing circuit 212. The amplified raw EEG signals 302a-302s may be converted by an ADC circuit to digital EEG signals and processed by the computer processing circuit to produce the plurality of digital EEG waveforms 300. The plurality of digital EEG waveforms 300 are provided first to the sleep stage detection algorithm 116 to decode the digital EEG waveforms 300 and to determine the subject's 102 stage of sleep. Upon detecting the sleep stage of the subject 102, the digital EEG waveforms 300 are provided to the transition events detection algorithm 118 to detect a down-state to up-state transition event 128 in a specific signal 126 of interest. Upon detection of the down-state to up-state transition event 128, the transition events detection algorithm 118 delivers an intervention signal 130 to the subject 102 via the neurostimulation electrodes 210a-d to improve memory replay for memories of events or tasks performed by the subject 102 prior to sleeping.

Figure 8:
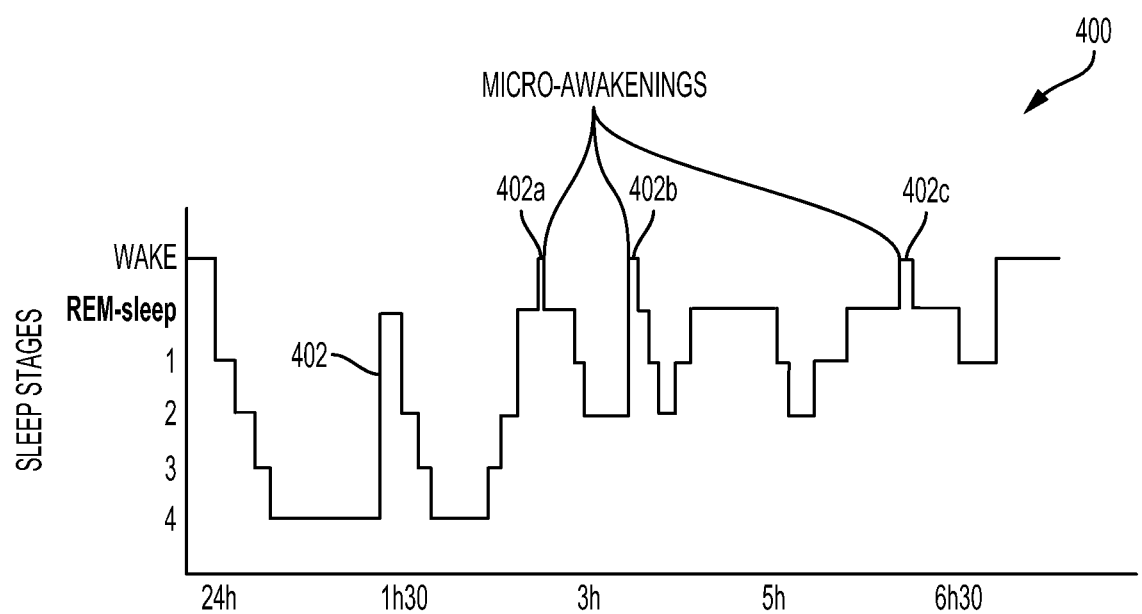
FIG. 8 depicts a hypnogram for determining the stages of sleep of a subject according to various aspects of the present disclosure.

FIG. 8 depicts a hypnogram 400 to determine the stages of sleep of a subject 102 according to various aspects of the present disclosure. The sleep stages are provided along the vertical axis and time is provided along the horizontal axis. As shown in FIG. 8, the sleep stages include wake stage, REM sleep stage, stage 1, stage 2, stage 3, and stage 4. As discussed above, stages 1 through 4 are considered NREM sleep. Other suitable classifications, such as a classification with only three stages of sleep, may also be used by the targeted memory enhancement system 200. Time is indicated at specific discrete points, including 24 hours, 1.5 hours, 3 hours, 5 hours, and 6.5 hours. The sleep stage detection algorithm 116 of the present disclosure detects in real time the stage of sleep of a subject. In one aspect, the sleep stage detection algorithm 116 generates the hypnogram 400 using a suitable polysomnography technique, which may include consideration of the weighted delta measure and normalized sigma measure described further with reference to FIGS. 10 and 11, for scoring or classifying the sleep stages as a function of time. A graph 402 represents the stages of sleep as a function of time. The hypnogram 400 provides an easy way to present the recordings of brain wave activity from a digital EEG waveform 114, 300 during a period of sleep. The graph 402 allows the different REM and NREM sleep to be identified during the sleep cycle of a subject. The transitions between various sleep stages may be identified as a function of time using the graph 402. Moreover, as shown in the hypnogram 400, the periods of micro-awakenings 402a, 402b, 402c are readily detectable. Micro-awakenings can occur during the period between the REM sleep state and the wake state. To generate the hypnogram 400, the sleep stage detection algorithm 116 also may involve monitoring parameters such as EEG, EOG, EMG as well as cardiopulmonary parameters such as electrocardiogram (ECG) and air flow. These monitored parameters also may be used to score or classify the sleep stages as a function of time. For example, a decreased tonic component in an EMG signal may be an indication of sleep stage 1. Additionally or alternatively, the computed weighted delta measure and normalized sigma measure may be used for sleep stage scoring.

FIG. 9 is a graphical depiction 500 of a specific EEG signal 502 of interest in a digital EEG waveform according to various aspects of the present disclosure. The vertical axis represents mean frontal potential (µV) and the horizontal axis represents time (s). As shown in FIG. 9, the mean frontal potential ranges from −120 to 40 µV and may correspond to EEG signals sensed by the first plurality of spatially separated EEG sensors 208a positioned near the frontal lobe. The time ranges from 0 seconds to 2 seconds. In one aspect, the specific EEG signal 502 of interest comprises a down-state-to-up-state transition event signal, which may be detected by the transition events detection algorithm 118. The detectable transition event is characterized by significant characteristics. In particular, the EEG signal 502 of interest has a negative edge 504 transition that indicates a steep potential voltage drop. As shown in FIG. 9, the negative edge 504 starts at approximately 0.8 seconds from a high potential of approximately 40 µV and ends at a low potential of approximately −110 µV. The transition events detection algorithm 118 may be configured to monitor a threshold mean frontal potential value for detection of a transition event. When the EEG signal 502 drops below a predetermined threshold 506, the transition events detection algorithm 118 determines that a down-state to up-state transition event 128 has occurred.

Although the predetermined threshold potential 506 is −80 μV in FIG. 9 (the −80 μV has been empirically determined during experiments to produce suitable results), other suitable thresholds may also be used. The threshold 506 may be empirically actively defined on the subject of a study by determining the variation in the signal 502 itself. For example, if a subject has a thick scalp or a thick skull that produces EEG signals 502 which are weaker than average, the transition events detection algorithm 118 may adjust the threshold 506 dynamically to compensate for the weaker EEG signals. After the EEG signal 502 drops below the threshold 506, it begins to rise again as indicated by the rising edge 508. As shown in FIG. 9, the rising edge 508 starts at approximately −110 μV and ends at the peak potential 510. The peak potential 510 is approximately 15 μV at 1.7 seconds. The detected transition event may be an indication that the hippocampus of the subject is ready for memory replay to reactivate and consolidate memory for long-term storage in the cortex. Specifically, the detected transition event may correspond to the interaction of cortical slow oscillations, thalamic sleep spindles and hippocampal SWR. The rising edge 508 can represent that the brain of the subject is increasing in excitability (higher neuroplasticity) to reach a depolarized cortical up-state in which interconnected neurons of a memory trace corresponding to a memory to be enhanced may be more likely to synchronously activate. The delivery of an intervention signal 130 may further increase the likelihood of synchronous activation. In contrast, the negative edge 504 can correspond to a polarized cortical down-state.

In another aspect, the computer processing circuit 212 may be configured to determine that the detection of a transition event is a false positive. When the transition events detection algorithm 118 detects that the negative edge 504 transition of the specific EEG signal 502 has crossed the −80 μV threshold 506, the transition events detection algorithm 118 determines whether the negative edge 504 transition of the specific EEG signal 502 initiated from a positive potential in order to mitigate false positives that, for example, can be due to drift in the EEG electrodes. In other words, a false positive may comprise the EEG signal 502 meandering aimlessly towards the negative potential because of bad grounding or some other similar reason. Thus, the false positive detection of the transition events detection algorithm 118 may reduce or prevent erroneously labeling the negative edge 504 transition of the EEG signal 502 a down-state to up-state transition event when the EEG signal 502 is a bad signal. Once the transition events detection algorithm 118 determines that the negative edge 504 transition crossed the threshold 506 within a narrow window of time and started from a positive potential, the transition events detection algorithm 118 determines that a down-state to up-state transition event 128 has occurred. The narrow window of time may be, for example, about 400 milliseconds (ms), starting 400 ms before the −80 μV threshold 506 crossing. There may also be a latency period between determination of the transition event before the intervention signal 130 is delivered. The latency period may be between 50 to 200 milliseconds (ms), such as 80 ms.

The determination by the transition events detection algorithm 118 that the EEG signal 502 initiated from a positive potential can indicate that there was a very sharp negative deflection in the specific EEG signal 502. This type of sharp negative deflection occurring during sleep stages 2 and 3 may almost always associated with a detectable down-state to up-state transition event 128. The brain may be constantly experiencing large scale oscillations (K-complexes in stage 2 and slow waves in stage 3). Accordingly, in sleep stage 2 or sleep stage 3, the transition events detection algorithm 118 is configured to detect exceptionally large transitions or slow oscillations of the EEG signal 502. Thus, the sleep stage detection algorithm 116 may determine a subject is in sleep stage 2 or 3 before sending a gate trigger to the transition events detection algorithm 118 to detect a transition event and deliver an intervention signal 130 upon detection of the transition event. Referring back to FIGS. 2-6, the transition events detection algorithm 118 may detect transition events 128 based on taking a spatial average of the first plurality of spatially separated frontal EEG channels 208a and determining a large negative change in mean frontal potential as shown in FIG. 9.

FIG. 10 is a flow diagram of a sleep stage detection algorithm 600 (which is similar to the sleep stage detection algorithm 116) according to various aspects of the present disclosure. The sleep stage detection algorithm 600 may employ high density EEG to enable reduction of noise through spatial averaging. Such noise reduction results in stronger EEG features sampled for better distinguishing differences in detected brain wave activity from different regions of the brain across sleep stages. In other words, noise reduction can enable the sensed EEG signals from the frontal channels corresponding to the first plurality of spatially separated EEG sensors 208a and the occipital channels corresponding to the second plurality of spatially separated EEG sensors 208b to be easily distinguishable. Additionally, the sensed EEG signals from the individual channels comprising the frontal channels and the occipital channels should be easily distinguishable. The frontal channels can comprise EEG sensors labeled Fz, F3 and F4. The occipital channels can comprise EEG sensors labeled Oz, O1, O2. In one aspect, the sleep stage detection algorithm 600 determines two spectral features for sleep stage classification. The first spectral feature is called a weighted delta measure ($D_w$) which is used for distinguishing between sleep stages 1 through 4. The second spectral feature comprises a multiplication ($\mu_N \cdot \sigma_N$) between normalized mean sigma power ($\mu_N$) and variance in sigma power ($\sigma_N$) for distinguishing between REM and NREM stages of sleep.

The second spectral feature $\mu_N \cdot \sigma_N$ may be calculated via measurements from central channels, which correspond to EEG sensors labeled Cz, C3, C4 that are positioned proximal to the central portion of the brain (i.e. the central sulcus or parietal lobe). EEG sensors Cz, C3 and C4 are not shown in FIGS. 1-6. The normalized variance sigma power $\sigma_N$ may also be used in isolation for distinguishing between REM and NREM stages of sleep. A threshold of 0.03 may be used such that if the $\sigma_N$ value is calculated to be less than the 0.03 threshold, the subject 102 is in a REM sleep stage. Furthermore, if the $\sigma_N$ value is calculated to be equal to or greater than the 0.03 threshold, the subject 102 may be determined to be in a NREM stage of sleep, such as sleep stage 2 or 3. In both determinations of the first and second spectral features, the sleep stages can be computed in 5 second time epochs and smoothed with a conservative approach to gate the transition events detection algorithm 118. The transition events detection algorithm 118 searches for the down-state to up-state transition events, as discussed above and shown in FIG. 9. Epoch containing arousals (high power across all EEG channels, which correspond to high power across all waveform frequency bands) are labeled as wake stage.

As shown in FIG. 10, in one aspect, the sleep stage detection algorithm 600 computes 602 the weighted delta measure $D_w$. $D_w$ can be calculated based on alpha, delta, and gamma power measurements from three frontal channels and three occipital channels. As described above, the headset 204 may include three frontal EEG sensors (channels Fz, F3, and F4) and three occipital EEG sensors (channels Oz, O1, and O2) for a total of 6 EEG channels. The three frontal EEG sensors form the first plurality of spatially separated sensors 208a and the three occipital EEG sensors form the second plurality of spatially separated EEG sensors 208b. In this aspect, the weighted delta measure $D_w$ may be calculated as the Delta Alpha Gamma ratio (DAG), where:

$$D_w = \frac{D}{A * G}$$

D=weighted delta power (0-4 Hz) over 3 frontal EEG channels
A=alpha power (8-13 Hz) over 3 occipital (back of head) EEG channels
G=gamma power (30-40 Hz) over all 6 EEG channels In another aspect, as discussed above, no occipital EEG sensors or channels are provided. As discussed above, alpha wave activity may not be prominent on frontal channels. Accordingly, in this aspect, $D_w$ can be calculated based only on delta and gamma power measurements from the three frontal channels (Fz, F3, and F4). Accordingly, $D_w$ may instead be calculated as the Delta Gamma ratio (DG), where:

$$D_w = \frac{D}{G}$$

D=weighted delta power (0-4 Hz) over 3 frontal EEG channels
G=gamma power (30-40 Hz) over the 3 frontal EEG channels As discussed above, additional or fewer EEG channels may be provided, as appropriate, for calculation of the weighted delta measure $D_w$ without departing from the spirit of the present disclosure. In sum, wake and all NREM stages can be classified or scored by the normalized measure $D_w$ (DAG) which is computed by dividing the weighted frontal delta power (Fz, F3, F4) by the product of the mean occipital alpha power (Oz, O1, O2) and the mean total gamma power (all EEG channels). Alternatively, wake and NREM stages can be classified or scored by $D_w$ (DG), computed by dividing the weighted frontal delta power (Fz, F3, F4) by the mean total gamma power (all EEG channels).

The DG or DAG is computed by taking a spectral power measure of the weighted delta power, where delta corresponds to EEG signals having very low frequencies in the range of 0 to 4 Hertz. After receiving the EEG signals from the three frontal EEG electrodes, the sleep stage detection algorithm 600 can compute the delta power from EEG signals between 0-4 Hz and segment the delta power measurement down into four separate frequencies (one, two, three, and four). This segmentation is done because the lower the frequency, the more likely that the subject 102 is in a deep stage of sleep. When the frequencies are segmented, a different weighting coefficient is applied to each one of the four sleep stages for calculation of the weighted delta measure. In the DG or DAG ratio, the alpha measure may be based on a measure of occipital alpha power (EEG signals between 8-13 Hz), determined based on the occipital EEG sensors placed at the back of the head. As the subject 102 transitions from a wake state to a sleep state, occipital alpha power decreases significantly. As described above, the global gamma measure (EEG signals having frequencies between 30-40 Hz) is computed across all EEG electrodes provided on the headset 204. Gamma is a rare frequency during sleep and is more commonly associated with rapid firing rates in brain cells during wake.

As shown in FIG. 10, once the weighted delta measure $D_w$ is calculated 602, if $D_w$ is ≤−0.05, the sleep stage is labeled 604 wake. If 0.05<$D_w$<=0.1, the sleep stage is labeled 606 stage 1. If 0.1<$D_w$≤0.2, the sleep stage is labeled 608 stage 2. If $D_w$>0.2, the sleep stage is labeled 610 stage 3. In sum, the $D_w$ thresholds for scoring sleep stages may be applied as follows: $D_w$ values less than or equal to 0.05 are classified as wake stage, $D_w$ values greater than 0.05 and less than or equal to 0.1 are classified as stage 1, $D_w$ values greater than 0.1 and less than or equal to 0.2 are classified as stage 2, $D_w$ values greater than 0.2 are classified as stage 3. When a four stage NREM classification is used, stage 4 may also be classified based on $D_w$ values greater than at least 0.2. The $D_w$ thresholds used here have been empirically determined as suitable for most subjects, but other suitable thresholds may be used as appropriate without departing from the scope of the present disclosure. As described above, the sleep stage detection algorithm 600 may also classify REM sleep by computing 612 the normalized sigma measure $\sigma_N$. If $\sigma_N$≥0.03, the sleep stage detection algorithm 600 determines that the subject 102 is a NREM stage and further determines whether the sleep stage is 2 or 3. If $\sigma_N$<0.03, the sleep stage of the subject 102 is labeled 614 as REM stage.

It is worthy to note that the down-state to up-state transition events of interest do not occur in REM stage sleep. Therefore, the consequence of a false positive from the standpoint of mislabeling a stage of sleep when it is actually REM is zero and no intervention signal 130 will be triggered. Accordingly, FIG. 11 is a flow diagram of a sleep stage detection algorithm 700 (similar to sleep stage detection algorithm 116 and 600) that does not check for REM sleep stage according to one aspect of the present disclosure. Accordingly, as shown in FIG. 11, the sleep stage of the subject 102 may be classified or scored only based on the weighted delta measure $D_w$, without any consideration of the normalized sigma measure $\sigma_N$. Thus, once the weighted delta measure $D_w$ is calculated 702, the $D_w$ thresholds as described in connection with FIG. 10 can be applied. Specifically, if $D_w$ is ≤−0.05 the sleep stage is labeled 704 wake. If 0.05<$D_w$≤0.1, the sleep stage is labeled 706 stage 1. If 0.1<$D_w$≤0.2 the sleep stage is labeled 708 stage 2. If $D_w$>0.2 the sleep stage is labeled 710 stage 3.

FIG. 12 illustrates an architectural or component view of a computing system 800 that may be employed with the memory replay process described in connection with FIGS. 1-11 according to various aspects of the present disclosure. For example, the computer processing circuit 212 described in the present disclosure may be part of such a computing system 800. In various aspects, as illustrated, the computing system 800 comprises one or more processors 802 (e.g., microprocessor, microcontroller, digital signal processor, logic circuits) coupled to various sensors 804 (e.g., EEG sensors, electrodes) and intervention signal generator 814 (e.g., neurostimulation electrodes, audio, visual, and the like) via a suitable driver 812 circuit. In addition, to the processor(s) 802, a storage device 806 (having operating logic 808) and communication interface 810, are coupled to each other as shown.

A computer processing circuit 800, shown in FIG. 12, comprises one or more microprocessor(s), digital signal processor, memory, input/output (I/O), analog-to-digital converter (ADC) circuits, digital-to-analog converter (DAC) circuits, and other features required of a functional computer to process EEG signals, execute the sleep stage detection algorithm 116, 600, 700, the down-state to up-state transition event detection algorithm 118, and deliver the intervention signal 130, among other functions. The computer processing circuit 800 receives inputs from the EEG sensors 208a-b, processes these signals and converts them into digital waveforms that may be employed by the sleep stage detection algorithm 116, 600, 700, and the transition event detection algorithm 118.

As described above, the EEG sensors 174 may be configured to detect and collect EEG signals from various locations of the head of the subject 102. As shown in FIGS. 1-7, the processor 802 processes the EEG signals data received from the EEG sensor(s) 804 to convert the signals with an ADC and execute the sleep stage detection algorithm 116, 600, 700 to determine the sleep stage of the subject 102. When the sleep stage is stage 2 or 3, the processor 802 executes the transition event detection algorithm 118 on the same data to determine whether a large negative potential transition has occurred. The intervention signal generator 814 applies an intervention signal 130 to the subject 102 via the driver 170 circuit. As discussed above, the intervention signal generator 814 may take many forms and in various aspects may include a neurostimulation signal, an audio signal, or other sensory stimulation. Accordingly, the computing system 800 may comprise a DAC to generate suitable intervention signals 130.

The processor 802 may be configured to execute the operating logic 808. The processor 802 may be any one of a number of single or multi-core processors known in the art. The storage 806 may comprise volatile and non-volatile storage media configured to store persistent and temporal (working) copies of the operating logic 808.

In various aspects, the operating logic 808 may be configured to process the collected EEG signals, such as the EEG signals 302a-s shown in FIG. 3, as described above. In various aspects, the operating logic 808 may be configured to perform the initial processing, and transmit the data, using wired or wireless media, to a separate host computer hosting the application to determine and generate instructions on the memory replay process described in connection with FIGS. 1-11. For these aspects, the operating logic 808 may be further configured to receive EEG signals from the subject and provide the processed EEG signals to a hosting computer. In alternate aspects, the operating logic 808 may be configured to assume a larger role in receiving the EEG signals. In either case, whether determined on its own or responsive to instructions from a hosting computer, the operating logic 808 may be further configured to control the intervention signal generator 814 to provide feedback to the subject when a transition event has been determined during sleep stages 2 or 3.

In various aspects, the operating logic 808 may be implemented in instructions supported by the instruction set architecture (ISA) of the processor 802, or in higher level languages and compiled into the supported ISA. The operating logic 808 may comprise one or more logic units or modules. The operating logic 88 may be implemented in an object oriented manner. The operating logic 808 may be configured to be executed in a multi-tasking and/or multi-thread manner. In other aspects, the operating logic 808 may be implemented in hardware such as a gate array.

In various aspects, the communication interface 810 may be configured to facilitate communication between a peripheral device and the computing system 800. The communication may include transmission of the collected EEG signals associated with the subject as described herein to a hosting computer, and transmission of data associated with the EEG signals from the host computer to the peripheral device. In various aspects, the communication interface 810 may be a wired or a wireless communication interface. An example of a wired communication interface may include, but is not limited to, a Universal Serial Bus (USB) interface. An example of a wireless communication interface may include, but is not limited to, a Bluetooth interface, Wi-Fi, or the like.

For various aspects, the processor 802 may be packaged together with the operating logic 808. In various aspects, the processor 802 may be packaged together with the operating logic 166 to form a System in Package (SiP). In various aspects, the processor 802 may be integrated on the same die with the operating logic 808. In various aspects, the processor 802 may be packaged together with the operating logic 808 to form a System on Chip (SoC).

Having shown and described various aspects of the present disclosure, further adaptations of the methods and systems described herein may be accomplished by appropriate modifications by one of ordinary skill in the art without departing from the scope of the present disclosure. Several of such potential modifications have been mentioned, and others will be apparent to those skilled in the art. For instance, the examples, aspects, geometrics, materials, dimensions, ratios, steps, and the like discussed above are illustrative and are not required. Accordingly, the scope of the present disclosure should be considered in terms of the following claims and is understood not to be limited to the details of structure and operation shown and described in the specification and drawings.

While various details have been set forth in the foregoing description, it will be appreciated that the various aspects of the system and method for using targeted memory enhancement during sleep may be practiced without these specific details. One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Further, while several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

For conciseness and clarity of disclosure, selected aspects of the foregoing disclosure have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing disclosure, it is appreciated that, throughout the foregoing disclosure, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one form, several portions of the subject matter described herein may be implemented via an application specific integrated circuits (ASIC), a field programmable gate array (FPGA), a digital signal processor (DSP), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In some instances, one or more elements may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other. It is to be understood that depicted architectures of different components contained within, or connected with, different other components are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated also can be viewed as being "operably connected," or "operably coupled," to each other to achieve the desired functionality, and any two components capable of being so associated also can be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In other instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present disclosure have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "one form," or "a form" means that a particular feature, structure, or characteristic described in connection with the aspect is included in at least one aspect. Thus, appearances of the phrases "in one aspect," "in an aspect," "in one form," or "in an form" in various places throughout the specification are not necessarily all referring to the same aspect. Furthermore, the particular features, structures or characteristics may be combined in any suitable manner in one or more aspects.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

Various aspects of the subject matter described herein are set out in the following examples.

1. A targeted method for memory enhancement, the method comprising: receiving, by a computer processing circuit, a plurality of electroencephalography (EEG) signals from a plurality of spatially separated EEG sensors located on the head of a subject that is asleep; determining, by a first process of the computer processing circuit, a sleep state of the subject; upon determining, by the computer processing circuit, based on a specific EEG signal that the sleep state of the subject is one of sleep stage 2 or sleep stage 3: triggering, by the computer processing circuit, a second process of the computer processing circuit; determining, by the second process of the computer processing circuit, a transition event of the specific EEG signal; and delivering, by the computer processing circuit, upon determining the transition event, an intervention signal to the subject designed to evoke a specific neurophysiological change to the subject.

2. The targeted method for memory enhancement method of Example 1, wherein determining, by the first process of the computer processing circuit, a sleep state of the subject, comprises: computing, by the computer processing circuit, a weighted delta measure ($D_w$) based on a plurality of EEG signals from a plurality of frontal EEG sensors and a plurality of EEG signals from a plurality of occipital EEG sensors.

3. The targeted method for memory enhancement method of Example 2, wherein computing, by the first process of the computer processing circuit, the weighted delta measure ($D_w$), comprises: computing, by the computer processing circuit, the weighted delta measure ($D_w$) based on the following expression:

$$D_w = \frac{D}{G}$$

wherein: D=weighted delta power over the plurality of frontal EEG signals; G=gamma power over the plurality of frontal EEG signals and the plurality of occipital EEG signals.

4. The targeted method for memory enhancement method of one or more of Examples 2 or 3, wherein the computation of the weighted delta measure ($D_w$) is based on the following expression:

$$D_w = \frac{D}{A*G}$$

wherein: D=weighted delta power over the plurality of frontal EEG signals; A=alpha power over the plurality of occipital EEG signals; G=gamma power over the plurality of frontal EEG signals and the plurality of occipital EEG signals.

5. The targeted method for memory enhancement method of one or more of Examples 2 through 4, comprising: determining, by the first process of the computer processing system, that the sleep state of the subject is a wake state, upon determining that the weighted delta measure $D_w$ fails to exceed 0.05.

6. The targeted method for memory enhancement method of one or more of Examples 2 through 5, comprising: determining, by the first process of the computer processing circuit, that the sleep state of the subject is a sleep stage 1, upon determining that the weighted delta measure $D_w$ falls within a range between 0.05 and 0.1.

7. The targeted method for memory enhancement method of one or more of Examples 2 through 6, comprising: determining, by the first process of the computer processing circuit, that the sleep state of the subject is the sleep stage 2, upon determining that the weighted delta measure $D_w$ exceeds 0.1 and fails to exceed 0.2.

8. The targeted method for memory enhancement method of one or more of Examples 2 through 6, comprising: computing, by the first process of the computer processing circuit, a normalized sigma measure, and determining one of sleep stage 2 or sleep stage 3, upon determining that the normalized sigma measure exceeds 0.03.

9. The targeted method for memory enhancement method of one or more of Examples 2 through 4 and 6 through 7, comprising: computing, by the first process of the computer processing circuit, a normalized sigma measure, and determining a rapid eye movement (REM) sleep state of the subject, upon determining that the normalized sigma measure fails to exceed 0.03.

10. The targeted method for memory enhancement method of Examples 7 or 8, comprising: determining, by the second process of the computer processing circuit, the transition event based on detecting a down-state to up-state transition when the specific EEG signal crosses below a predetermined threshold.

11. The targeted method for memory enhancement method of Example 10, comprising: determining, by the second process of the computer processing circuit, that the negative edge transition of the specific EEG signal initiates from a positive potential.

12. A system for targeted memory enhancement, the system comprising: a plurality of spatially separated EEG sensors configured to be located on the head of a subject to generate a plurality of electroencephalography (EEG) signals; and a computer processing circuit configured to receive the plurality of EEG signals and to deliver an intervention signal designed to evoke a specific neurophysiological change to the subject based on a determined transition event, wherein the computer processing circuit is further configured to: determine that the subject is in one of a sleep stage 2 or a sleep stage 3 based on a specific EEG signal of the plurality of EEG signals, determine the transition event, wherein the transition event occurs during one of the sleep stage 2 or the sleep stage 3.

13. The system for targeted memory enhancement of Example 12, wherein the computer processing circuit is further configured to determine the transition event based on detecting a down-state to up-state transition of the specific EEG signal when a positive edge transition of the specific EEG signal succeeds a negative edge transition of the specific EEG signal.

14. The system for targeted memory enhancement of Example 12 or 13, wherein the computer processing circuit is further configured to determine that the subject is in one of a sleep stage 2 or a sleep stage 3 based on a specific EEG signal of the plurality of EEG signals by computing a weighted delta measure ($D_w$) based on the following expression:

$$D_w = \frac{D}{G}$$

wherein: D=weighted delta power over the plurality of frontal EEG signals; G=gamma power over the plurality of frontal EEG signals and the plurality of occipital EEG signals.

15. The system for targeted memory enhancement of one or more Examples 12 through 14, wherein the computation of the weighted delta measure ($D_w$) is based on the following expression:

$$D_w = \frac{D}{A*G}$$

wherein: D=weighted delta power over the plurality of frontal EEG signals; A=alpha power over the plurality of occipital EEG signals; G=gamma power over the plurality of frontal EEG signals and the plurality of occipital EEG signals.

16. The system for targeted memory enhancement of one or more Examples 12 through 15, wherein the computer processing circuit is further configured to deliver an electrical current to an area of a brain of the subject.

17. The system for targeted memory enhancement of one or more Examples 12 through 16, wherein the computer processing circuit is further configured to deliver a sensory stimulation that is associated with a specific memory of the subject.

18. A targeted memory enhancement apparatus comprising: a plurality of spatially separated electroencephalography (EEG) sensors configured to be located on the head of a subject, wherein the spatially separated EEG sensors are further configured to generate a plurality of EEG signals, wherein the plurality of spatially separated EEG sensors is for use with a targeted memory enhancement method, and wherein the targeted memory enhancement method comprises: determining the subject is in one of a sleep stage 2 or a sleep stage 3 based on a specific EEG signal; determining a neural biomarker of the specific EEG signal; and delivering, upon determining the neural biomarker, an intervention signal to the subject designed to evoke a specific neurophysiological change to the subject.

19. The targeted memory enhancement apparatus of Example 18, wherein determining a neural biomarker of the specific EEG signal comprises determining a transition event based on detecting a down-state to up-state transition of the specific EEG signal when a positive edge transition of the specific EEG signal succeeds a negative edge transition of the specific EEG signal.

20. The targeted memory enhancement apparatus of Examples 18 or 19, wherein determining the subject is in one of sleep stage 2 or sleep stage 3 based on a specific EEG signal comprises the computer processing circuit computing a weighted delta measure ($D_w$) based on the following expression:

$$D_w = \frac{D}{G}$$

wherein: D=weighted delta power over the plurality of frontal EEG signals; G=gamma power over all EEG signals.

The invention claimed is:

1. A targeted method for memory enhancement, the method comprising:
receiving, by a computer processing circuit, a plurality of electroencephalography (EEG) signals from a plurality of spatially separated EEG sensors located on the head of a subject that is asleep;
determining, by a first process of the computer processing circuit, a sleep state of the subject, comprising:
computing, by the computer processing circuit, a weighted delta measure (Dw) based on a plurality of EEG signals from a plurality of frontal EEG sensors and a plurality of EEG signals from a plurality of occipital EEG sensors wherein the weighted delta measure ($D_w$) is based on the following expression:

$$D_w = \frac{D}{G}$$

wherein:
D=weighted delta power over the plurality of frontal EEG signals;
G=gamma power over the plurality of frontal EEG signals and the plurality of occipital EEG signals;
upon determining, by the computer processing circuit, based on a specific EEG signal that the sleep state of the subject is one of sleep stage 2 or sleep stage 3:
triggering, by the computer processing circuit, a second process of the computer processing circuit;
determining, by the second process of the computer processing circuit, a transition event of the specific EEG signal; and
delivering, by the computer processing circuit, upon determining the transition event, an intervention signal to the subject designed to evoke a specific neurophysiological change to the subject.

2. The targeted method for memory enhancement method of claim 1, wherein the computation of the weighted delta measure ($D_w$) is based on the following expression:

$$D_w = \frac{D}{A*G}$$

wherein:
D=weighted delta power over the plurality of frontal EEG signals;
A=alpha power over the plurality of occipital EEG signals;
G=gamma power over the plurality of frontal EEG signals and the plurality of occipital EEG signals.

3. The targeted method for memory enhancement method of claim 2, comprising:
determining, by the first process of the computer processing system, that the sleep state of the subject is a wake state, upon determining that the weighted delta measure $D_w$ fails to exceed 0.05.

4. The targeted method for memory enhancement method of claim 2, comprising:

determining, by the first process of the computer processing circuit, that the sleep state of the subject is a sleep stage 1, upon determining that the weighted delta measure $D_w$ falls within a range between 0.05 and 0.1.

5. The targeted method for memory enhancement method of claim 2, comprising:
determining, by the first process of the computer processing circuit, that the sleep state of the subject is the sleep stage 2, upon determining that the weighted delta measure $D_w$ exceeds 0.1 and fails to exceed 0.2.

6. The targeted method for memory enhancement method of claim 5, comprising:
determining, by the second process of the computer processing circuit, the transition event based on detecting a down-state to up-state transition when the specific EEG signal crosses below a predetermined threshold.

7. The targeted method for memory enhancement method of claim 6, comprising:
determining, by the second process of the computer processing circuit, that the negative edge transition of the specific EEG signal initiates from a positive potential.

8. The targeted method for memory enhancement method of claim 2, comprising:
computing, by the first process of the computer processing circuit, a normalized sigma measure, and determining one of sleep stage 2 or sleep stage 3, upon determining that the normalized sigma measure exceeds 0.03,
wherein the normalized sigma measure is a product of a normalized mean sigma power and a variance in the sigma power, and
wherein the sigma power is calculated from measurements of signals obtained from central EEG sensor channels positioned proximal to a central sulcus or parietal lobe located on the head of the subject.

9. The targeted method for memory enhancement method of claim 2, comprising:
computing, by the first process of the computer processing circuit, a normalized sigma measure, and determining a rapid eye movement (REM) sleep state of the subject, upon determining that the normalized sigma measure fails to exceed 0.03,
wherein the normalized sigma measure is a product of a normalized mean sigma power and a variance in the sigma power, and
wherein the sigma power is calculated from measurements of signals obtained from central EEG sensor channels positioned proximal to a central sulcus or parietal lobe located on the head of the subject.

10. A system for targeted memory enhancement, the system comprising:
a plurality of spatially separated EEG sensors configured to be located on the head of a subject to generate a plurality of electroencephalography (EEG) signals; and
a computer processing circuit configured to receive the plurality of EEG signals and to deliver an intervention signal designed to evoke a specific neurophysiological change to the subject based on a determined transition event, wherein the computer processing circuit is further configured to:
determine that the subject is in one of a sleep stage 2 or a sleep stage 3 based on a specific EEG signal of the plurality of EEG signals, by computing a weighted delta measure ($D_w$) based on the following expression:

$$D_w = \frac{D}{G}$$

wherein:
D=weighted delta power over the plurality of frontal EEG signals;
G=gamma power over the plurality of frontal EEG signals and the plurality of occipital EEG signals; and
determine the transition event, wherein the transition event occurs during one of the sleep stage 2 or the sleep stage 3.

11. The system for targeted memory enhancement of claim 10, wherein the computer processing circuit is further configured to determine the transition event based on detecting a down-state to up-state transition of the specific EEG signal when a positive edge transition of the specific EEG signal succeeds a negative edge transition of the specific EEG signal.

12. The system for targeted memory enhancement of claim 10, wherein the computation of the weighted delta measure (Dw) is based on the following expression:

$$D_w = \frac{D}{A * G}$$

wherein:
D=weighted delta power over the plurality of frontal EEG signals;
A=alpha power over the plurality of occipital EEG signals;
G=gamma power over the plurality of frontal EEG signals and the plurality of occipital EEG signals.

13. The system for targeted memory enhancement of claim 10, wherein the computer processing circuit is further configured to deliver an electrical current to an area of a brain of the subject.

14. The system for targeted memory enhancement of claim 10, wherein the computer processing circuit is further configured to deliver a sensory stimulation that is associated with a specific memory of the subject.

15. A targeted memory enhancement apparatus comprising:
a plurality of spatially separated electroencephalography (EEG) sensors configured to be located on the head of a subject wherein the spatially separated EEG sensors are further configured to generate a plurality of EEG signals;
a computer processing circuit configured to receive the plurality of electroencephalography (EEG) signals from the plurality of spatially separated EEG sensors; and
a memory device configured to store instructions to be executed by the computer processing circuit,
wherein the instructions comprise a targeted memory enhancement method, and wherein the instructions, when executed by the computer processing circuit, causes the computer processing circuit to:
determine that the subject is in one of a sleep stage 2 or a sleep stage 3 based on a specific EEG signal by computing a weighted delta measure ($D_w$) based on the following expression:

$$D_w = \frac{D}{G}$$

wherein:
D=weighted delta power over the plurality of frontal EEG signals;
G=gamma power over all EEG signals;
determine a neural biomarker of the specific EEG signal; and
deliver, upon determining the neural biomarker, an intervention signal to the subject designed to evoke a specific neurophysiological change to the subject.

16. The targeted memory enhancement apparatus of claim 15, wherein the determination of a neural biomarker of the specific EEG signal comprises a determination of a transition event based on detecting a down-state to up-state transition of the specific EEG signal when a positive edge transition of the specific EEG signal succeeds a negative edge transition of the specific EEG signal.

* * * * *